(12) United States Patent
Dobson et al.

(10) Patent No.: US 11,730,971 B2
(45) Date of Patent: *Aug. 22, 2023

(54) MAGNETIC PARTICLE CONJUGATES AND METHODS OF ACTIVATING CELL SIGNALING

(71) Applicant: University of Florida Research Foundation, Inc., Gainesville, FL (US)

(72) Inventors: Jon P. Dobson, Gainesville, FL (US); Josephine Allen, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 436 days.

This patent is subject to a terminal disclaimer.

(21) Appl. No.: 16/941,181

(22) Filed: Jul. 28, 2020

(65) Prior Publication Data

US 2020/0353276 A1  Nov. 12, 2020

Related U.S. Application Data

(63) Continuation of application No. 16/061,848, filed as application No. PCT/US2017/012280 on Jan. 5, 2017, now Pat. No. 10,765,881.

(60) Provisional application No. 62/276,416, filed on Jan. 8, 2016.

(51) Int. Cl.
*A61N 2/02*  (2006.01)
*C12N 15/115*  (2010.01)
*A61N 2/00*  (2006.01)
*A61N 2/06*  (2006.01)

(52) U.S. Cl.
CPC ............... *A61N 2/02* (2013.01); *A61N 2/002* (2013.01); *A61N 2/06* (2013.01); *C12N 15/115* (2013.01); *C12N 2310/16* (2013.01); *C12N 2310/351* (2013.01)

(58) Field of Classification Search
CPC . A61N 2/02; A61N 2/002; A61N 2/06; C12N 15/115; C12N 2310/16; C12N 2310/351
USPC ....................................................... 600/9–15
See application file for complete search history.

(56) References Cited

U.S. PATENT DOCUMENTS

| | | | |
|---|---|---|---|
| 8,651,113 B2 | 2/2014 | Seeney et al. | |
| 10,765,881 B2 * | 9/2020 | Dobson | A61N 2/06 |
| 2003/0219801 A1 | 11/2003 | Lipshutz | |
| 2005/0090732 A1 | 4/2005 | Ivkov et al. | |
| 2008/0268061 A1 | 10/2008 | Jordan et al. | |
| 2010/0119492 A1 | 5/2010 | Hans et al. | |

(Continued)

FOREIGN PATENT DOCUMENTS

WO 2014167126 A2 10/2014

OTHER PUBLICATIONS

Stemedica Cell Technologies, Inc. (San Diego, California) URL: http://www.stemedica.com, Mar. 28, 2007; accessed via http://web.archive.org on Aug. 14, 2018, 1 page.

(Continued)

*Primary Examiner* — Sunita Reddy
(74) *Attorney, Agent, or Firm* — Thomas Horstemeyer, LLP

(57) ABSTRACT

Embodiments of the present disclosure provide for magnetic particle conjugates, methods of making the magnetic particle conjugates, methods of using magnetic particle conjugates, and the like.

8 Claims, 4 Drawing Sheets

(56) References Cited

U.S. PATENT DOCUMENTS

| | | | |
|---|---|---|---|
| 2011/0052672 A1* | 3/2011 | Krishnan | A61K 47/60 |
| | | | 424/93.4 |
| 2011/0130616 A1* | 6/2011 | Seeney | A61K 9/5094 |
| | | | 424/490 |
| 2014/0052020 A1* | 2/2014 | Allen | A61B 10/00 |
| | | | 600/562 |

OTHER PUBLICATIONS

Organogenesis, Inc. (Canton, Massachusetts) URL: http://www.organogenesis.com, Feb. 12, 1998; accessed via http://web.archive.org on Aug. 14, 2018, 1 page.

MICA BioSystems (Solihull, West Midlands, England) URL: http://micabiosystems.com, Sep. 28, 2015; accessed via http://web.archive.org on Aug. 14, 2018, 1 page.

Kim, B. et al., Aptamer-modified magnetic nanoprobe for molecular MR imaging ofVEGFR2 on angiogenic vasculature. Nanoscale Research Letters 2013, 8:399, Sep. 26, 2013; abstract, pp. 2-4,6, figure 6.

Hu, B. et al. Receptor-Targeted, Magneto-Mechanical Stimulation of Osteogenic Differentiation of Human Bone Marrow-Derived Mesenchymal Stem Cells. Int. J. Mol. Sci. 2013, 14, 19276-19293, Sep. 23, 2013; pp. 19277,19287, figure 5.

International Search Report for application No. PCT/US17/12280, dated Mar. 16, 2017, 12 pages.

\* cited by examiner

MAGNETIC PARTICLE CONJUGATES AND METHODS OF ACTIVATING CELL SIGNALING

CROSS-REFERENCE TO RELATED APPLICATIONS

This application is a continuation of co-pending U.S. patent application Ser. No. 16/061,848, filed on Jun. 13, 2018, entitled "MAGNETIC PARTICLE CONJUGATES AND METHODS OF ACTIVATING CELL SIGNALING," which is the 35 U.S.C. § 371 national stage application of PCT Application No. PCT/US2017/012280, filed on Jan. 5, 2017, where the PCT claims the benefit of and priority to U.S. Provisional Patent Application No. 62/276,416, filed on Jan. 8, 2016, entitled "MAGNETIC PARTICLE CONJUGATES AND METHODS OF ACTIVATING CELL SIGNALING."

The contents of U.S. Ser. No. 16/061,848, PCT/US2017/012280, and U.S. Ser. No. 62/276,416 are incorporated herein by reference in their entirety.

BACKGROUND

Many receptor ligands used in the control of receptor-mediated cell processes create unwanted effects including activation of non-specific receptors or binding to non-specific cell types. Presently, there is a need in the art for targeted therapeutic agents that selectively activate cell surface receptors.

SUMMARY

Embodiments of the present disclosure provide for magnetic particle conjugates, methods of making the magnetic particle conjugates, methods of using magnetic particle conjugates, and the like.

An embodiment of the present disclosure includes a method of activating cell signaling that includes: introducing a magnetic particle conjugate to a subject, wherein the magnetic particle conjugate includes a magnetic core and a nucleic acid aptamer attached to the magnetic core, wherein the aptamer has an affinity for a target cell, wherein the magnetic particle conjugate binds to the target cell; and subjecting the magnetic particle conjugate to a magnetic field, wherein application of the magnetic field causes an energy transfer to the target cell activating a specific biochemical signaling cascade in the target cell. In an embodiment, activating cell signaling is caused by transferring energy from the magnetic field to the magnetic particle and inducing a conformational change in the target cell's receptor. The method can be performed in vitro or in vivo.

Embodiments of the present disclosure provide for a composition having a magnetic particle conjugate that includes a magnetic core and a nucleic acid aptamer attached to the magnetic core, wherein the aptamer has an affinity for a target cell. In an embodiment, the nucleic acid aptamer can include aptamers targeting one or more of the following: transforming growth factor-β receptor, vascular endothelial growth factor receptor, bone morphogenic protein receptor, and voltage-gated, ligand-gated or mechanosensitive ion channels. In an embodiment, the magnetic core can include: $Fe_3O_4$, $\gamma Fe_2O_3$, $\alpha Fe_2O_3$, iron sulfide, strontium ferrite, barium ferrite, and cobalt ferrite.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
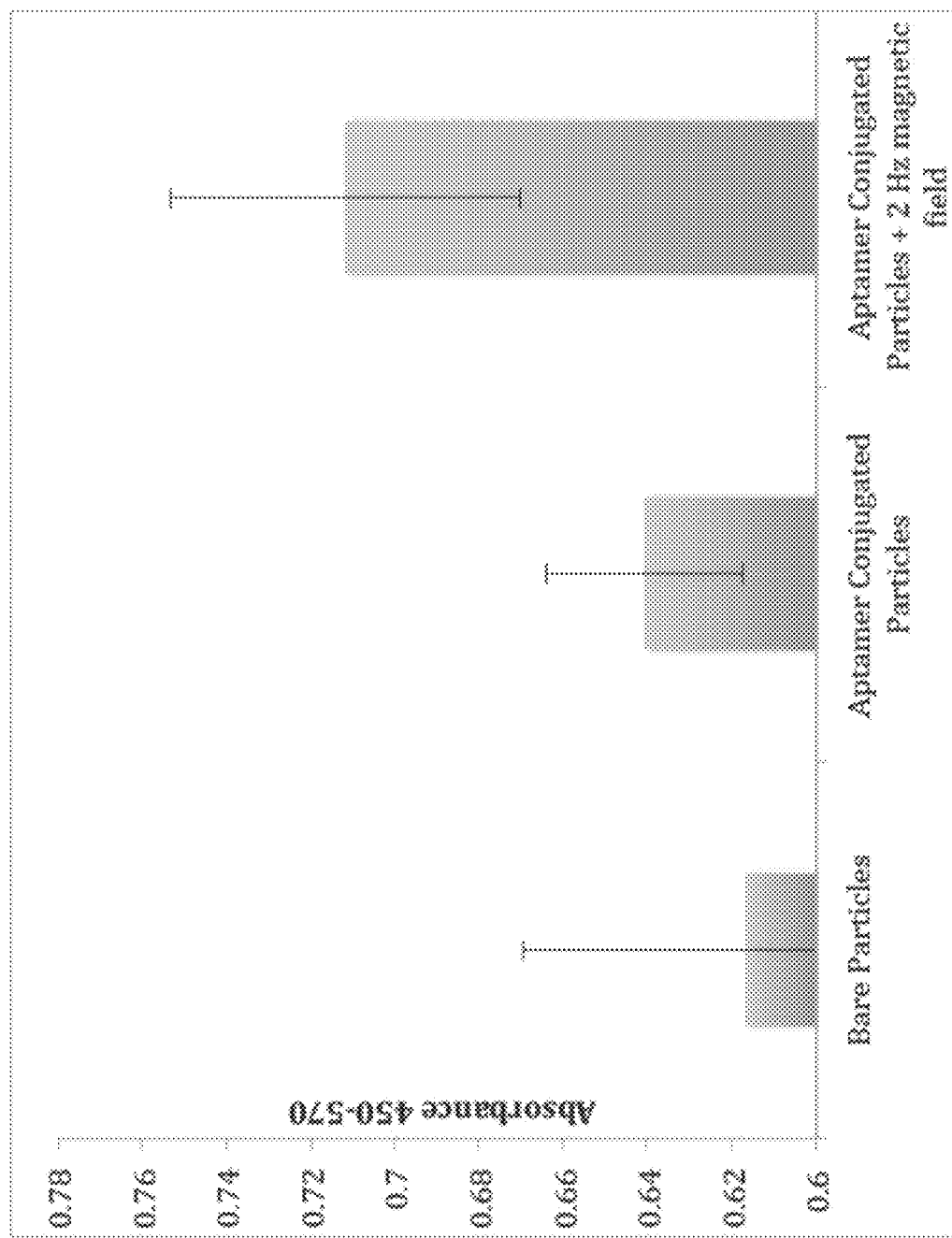
FIG. 1 shows Phosphorylation (activation) of VEGFR2 in HUVECs: Magnefect™ horizontal oscillating field/6-well NdFeB magnet array/20 min. (N=3), using magnetic particles with no VEGF aptamer conjugation, VEGF aptamer-functionalized magnetic particles with no field, and VEGF aptamer-functionalized particles with an applied field.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of biochemistry, microbiology, molecular biology, pharmacology, medicine, and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions:

By "administration" is meant introducing a magnetic particle conjugate of the present disclosure into a subject or cell or tissue sample. The route of administration can include any route of administration, such as intravenous oral, topical, subcutaneous, peritoneal, intraarterial, inhalation, vaginal, rectal, nasal, introduction into the cerebrospinal fluid, or instillation into body compartments can be used.

The terms "therapeutically effective amount" and "an effective amount" are used interchangeably herein and refer to that amount of the magnetic particle conjugate being administered that is sufficient to affect the intended result. For example, an effective amount of the magnetic particle conjugate can activate cell signaling upon application of a magnetic field. The therapeutically effective amount may vary depending upon the intended application (in vitro or in vivo), or the subject, e.g., the weight and age of the subject, the manner of administration and the like, which can readily be determined by one of ordinary skill in the art. The specific dose will vary depending on the particular agent chosen, the dosing regimen to be followed, whether it is administered in combination with other agents, timing of administration, and the physical delivery system in which it is carried.

The term "unit dosage form," as used herein, refers to physically discrete units suitable as unitary dosages for human and/or animal subjects, each unit containing a predetermined quantity of the magnetic particle conjugate calculated in an amount sufficient to produce the desired effect in association with a pharmaceutically acceptable diluent, carrier or vehicle. The specifications for unit dosage forms depend on the particular magnetic particle conjugate employed, the route and frequency of administration, and the effect to be achieved, and the pharmacodynamics associated with each magnetic particle conjugate in the subject.

As used herein, a "pharmaceutical composition" and a "pharmaceutical formulation" are meant to encompass embodiments of the present disclosure suitable for administration to a subject, such as a mammal, especially a human. In general, a "pharmaceutical composition" or "pharmaceutical formulation" is sterile, and preferably free of contaminants that are capable of eliciting an undesirable response within the subject (e.g., the magnetic particle conjugate in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

As used herein, the terms "treatment", "treating", and "treat" are defined as to achieve a desired result (activate cell signaling) using magnetic particle conjugates. "Treatment", as used herein, covers any treatment in a subject (e.g., a mammal, typically a human or non-human animal of veterinary interest).

As used herein, the term "subject" includes humans, mammals (e.g., cats, dogs, horses, etc.), birds, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, cell or tissue samples, or blood, urine, or tissue samples of the animals mentioned for veterinary applications. In some embodiments, a system includes a sample and a host. The term "living host" refers to the entire host or organism and not just a part excised (e.g., a liver or other organ) from the living host.

The terms "VEGF receptor" or "VEGFR" as used herein, are receptors for vascular endothelial growth factors. The terms may encompass the various types and subtypes of VEGF receptors (e.g. VEGFR-1, VEGFR-2, VEGFR-3, mbVEGFR, sVEGFR, etc.).

Discussion:

Embodiments of the present disclosure provide for magnetic particle conjugates, methods of making the magnetic particle conjugates, methods of using magnetic particle conjugates, and the like. Embodiments of the present disclosure can be used to stimulate target cells by affecting the cell signaling receptors of the target cells. It is advantageous in tissue engineering and regenerative medicine to control cell signaling for stem cell differentiation or tissue matrix production. In this regard, embodiments of the present disclosure can be used in vitro, ex vivo and/or in vivo for stem cell therapies or tissue generation technologies.

Embodiments of the present disclosure include a magnetic particle conjugate having a magnetic core and a nucleic acid aptamer. The nucleic acid aptamer can be attached (directly or indirectly) to the magnetic core. The term "bind" or "bound" can refer to, but is not limited to, chemically bonded (e.g., covalently or ionically), biologically bonded, biochemically bonded, and/or otherwise associated with the material. In an embodiment, being bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, Tr-Tr stacking interactions, combinations thereof, and like interactions. In an embodiment the magnetic core can include a linker and/or coating so that the aptamer can bind to the magnetic core.

In an embodiment, the magnetic core has a magnetic moment strong enough to accomplish the desired result (e.g., to stimulate target cells by affecting the cell signaling receptors). In an embodiment, the magnetic core can be: iron oxide, $Fe_3O_4$, $\gamma Fe_2O_3$, or $\alpha Fe_2O_3$ as well as cobalt ferrite ($CoFe_2O_4$), barium ferrite ($BaFe_{12}O_{19}$), strontium ferrite ($SrFe_{12}O_{19}$), and iron sulfide (FeS). In an embodiment, the magnetic core can have a diameter on the micro-scale (e.g., about 500 nm to 900 nm) or nano-scale (e.g., about 10 to 500 nm).

The aptamer has an affinity for a target cell, in particular for specific cell surface receptors of the target cell. "Affinity" as used herein refers to the aptamer having a stronger attraction towards the targeted cell or more specifically a receptor(s) of the target cell relative to other cells or receptors on the cell. The aptamer can be designed or selected based on the cell surface receptor to be targeted. In an embodiment, the aptamer does not activate the cell surface receptor upon binding with the cell surface receptor or does not activate the cell surface receptor in such a way as to achieve the desired results (e.g., the results achieved by activation via applying a magnetic field to the magnetic particle conjugate). In an embodiment, the nucleic acid aptamer can be one of the following aptamers: transforming growth factor-β receptor, platelet-derived growth factor receptor, and ligand, vascular endothelial growth factor receptor, bone morphogenic protein receptor, voltage-gated, ligand-gated or mechanosensitive ion channels.

As described above, embodiments of the present disclosure use nucleic acid aptamers conjugated to magnetic cores as targeting agents for target cells, specifically surface cell receptors. By binding the aptamer that has been screened to target a specific receptor to a magnetic particle, embodiments of the present disclosure provide for the ability to apply external magnetic fields onto the magnetic particle conjugate to remotely transfer energy to the magnetic particle conjugate and the receptor to which it is attached. This transfer of energy may be either mechanical, such as by a static magnetic field with a field gradient or by oscillating the field at low frequencies, and/or, potentially, thermal, by using radiofrequency fields to induce hyperthermia effects. By activating cell surface receptors in this manner, it will be possible to remotely control cell signaling and associated behavior such as apoptosis, cell division, motility, stem cell differentiation and tissue formation. As mentioned above, aptamers are ideal targeting molecules as they can be designed to target very specific receptors and, in many cases, binding of the aptamer to the receptor does not in itself activate the receptor, which is not always the case with other targeting molecules such as proteins, peptides and antibodies.

In regard to the method of activating cell signaling, the method can be accomplished by introducing (e.g., administering) the magnetic particle conjugate to a subject. The magnetic particle will bond with the target cell via the aptamer. After an appropriate amount of time, the subject or a portion of the subject is subjected to a magnetic field. In an embodiment, the magnetic field can be periodically applied or pulsed. In an embodiment, the magnetic field can be applied at certain times of the day. The term "periodically" refers to applying the magnetic field at established time frames that may be at regular or irregular time intervals on the time frames of seconds, hours, days, weeks, or months (e.g., about 1 s to 2 months, about 1 hour to 1 day, about 1 day to 1 month, or other the like) depending upon the specific circumstances. In an embodiment, the impulses of the magnetic field can last on the time frame of milliseconds, seconds, hours, or days (e.g., about 1 millisecond to 1 day, about 10 seconds to 1 hour, about 1 minute to 12 hours, about 1 hour to 1 day, or the like) depending upon the specific circumstances. The time frame and duration of magnetic field can be designed based on particular circumstances and requirements of a specific situation.

Application of the magnetic field causes an energy transfer to the target cell activating a specific biochemical signaling cascade in the target cell. The transfer of energy from the magnetic field to the magnetic particle conjugate can induce a conformational change in the target cell, specifically a selected cell surface receptor(s). In an embodiment, the conformation change in cell surface receptor can causes one of the following: apoptosis, cell division, motility, stem cell differentiation, activation of a neuronal action potential, blocking of a neuronal action potential, or tissue formation. In an embodiment, the hyperthermia induces a conformation change in the cell surface receptors.

In an embodiment, the magnetic field can be generated by electrically conducting coils connected to a power source, or by high-gradient permanent magnets or magnetic materials such as NdFeB or SmCo magnets or by magnetic fields induced in soft magnetic materials, such as permalloy, via a surrounding coil or by coming into contact with a permanent magnet.

In an embodiment, the magnetic particle conjugate can optionally include one or more agents (e.g., a chemical or biological agent), where the agent can be disposed indirectly or directly on the magnetic particle conjugate. In general, the agent can be bound to the magnetic particle conjugate by a physical, biological, biochemical, and/or chemical association directly or indirectly by a suitable means. The agent can be administered to the subject to treat, image, detect, study, monitor, and/or evaluate a condition or an occurrence, or the like in the subject. In an embodiment, the agent can include, but is not limited to, a drug, a therapeutic agent, a radiological agent, a small molecule drug, a biological agent (e.g., polypeptides (e.g., proteins such as, but not limited to, antibodies (monoclonal or polyclonal)), antigens, nucleic acids (both monomeric and oligomeric), polysaccharides, haptens, sugars, fatty acids, steroids, purines, pyrimidines, ligands, and aptamers) and combinations thereof, that can be used to image, detect, study, monitor, evaluate, and the like. In an embodiment, the agent is included in an effective amount to accomplish its purpose, where such factors to accomplish the purpose are well known in the medical arts.

Embodiments of the present disclosure may be useful for developing dynamic drug screening tools for applications such as ion channel drugs.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLE

FIG. 1 shows phosphorylation of the vascular endothelial growth factor recpetor in human umbilical vein endothelial cells in repsonse to (from left to right) exposure to magnetic nanoparticles without any aptamer attached, exposure to particles with the aptamer targeting VEGF receptor attached but with no applied magnetic field, and exposure to particles with the aptamer targeting VEGF receptor and the application of a 2 Hz oscillating magnetic field.

Figure 2:
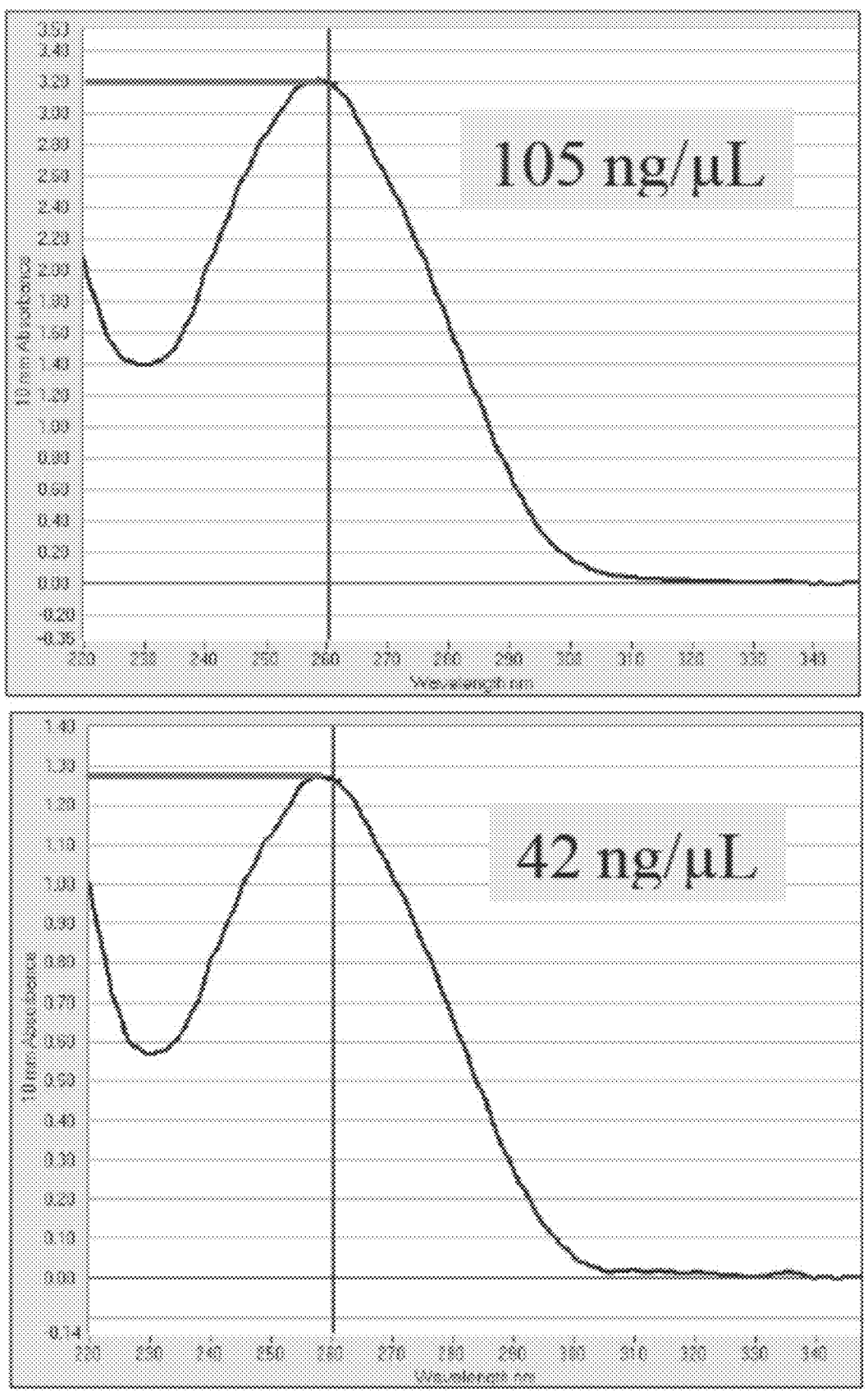
FIG. 2 illustrates the supernatant aptamer concentration pre- and post-conjugation via fluorescence absorbance showing a concentration of 105 ng/μL of VEGF aptamer in the supernatant before conjugation and 42 ng/μL after conjugation, indication more than half or the VEGF aptamer in the supernatant is bound to the particles.

FIG. 2 illustrates the supernatant aptamer concentration pre- and post-conjugation.

Figure 3:
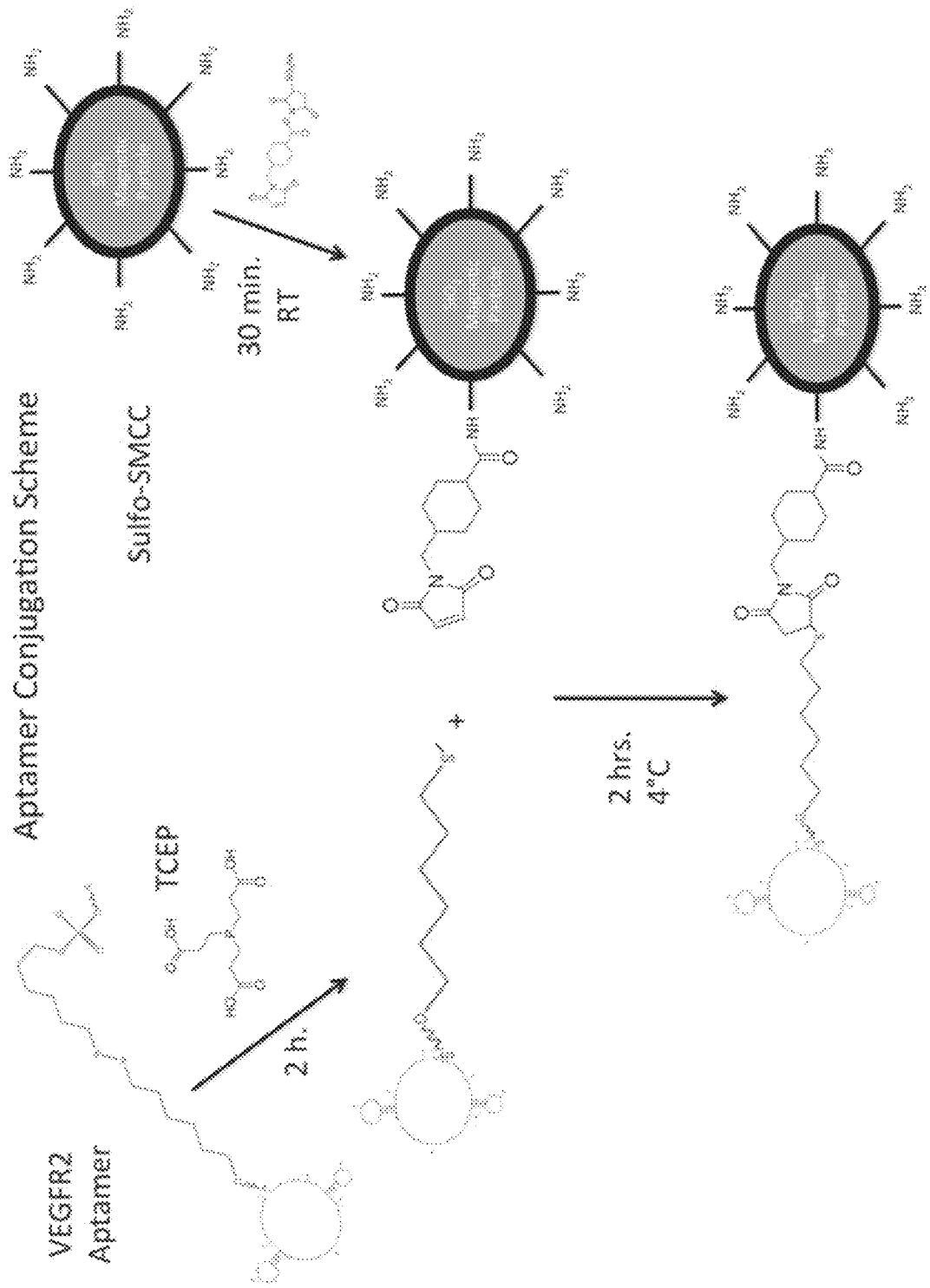
FIG. 3 illustrates the schematic example of aptamer conjugation to $NH_2$-functionalized $SiO_2$-coated iron oxide nanoparticles using a sulfo-SMCC conjugation chemistry strategy.

FIG. 3 illustrates the schematic example of aptamer conjugation to NH$_2$-functionalized SiO$_2$-coated iron oxide nanoparticles.

Figure 4:
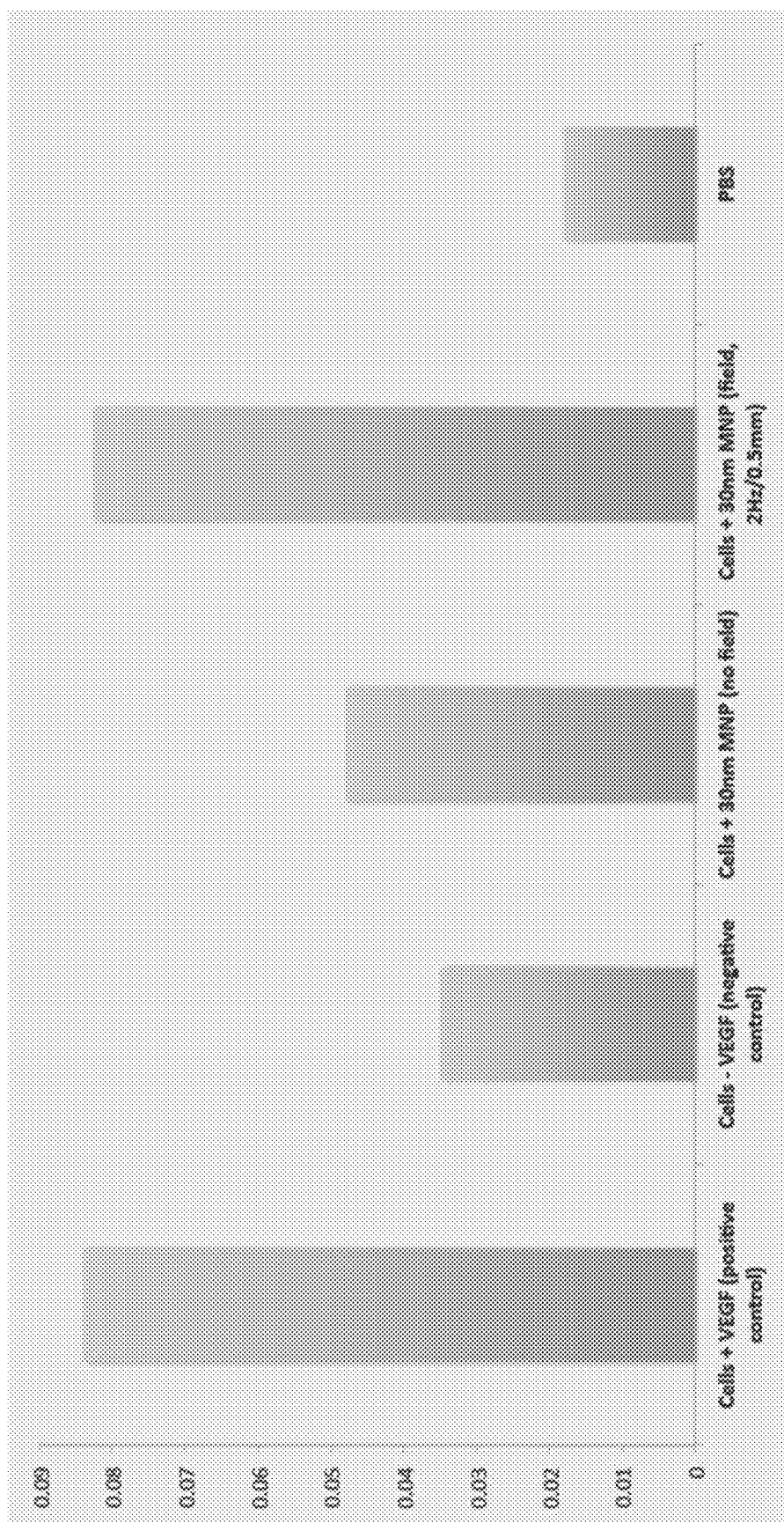
FIG. 4 is a VEGFR phosphorylation assay as in FIG. 1 with the addition of a positive control and a phosphate buffer sample group.

FIG. 4 is a VEGFR phosphorylation assay, demonstrating a trend towards activation of the VEGF receptor. The Cells+30 nm MNP (field, 2 Hz/0.5 mm) is the magnetic activation of the magnetic nanoparticles conjugated with the VEGF receptor-targeting aptamer.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A method of activating cell signaling, comprising:
   introducing a magnetic particle conjugate to a subject, wherein the magnetic particle conjugate includes a magnetic core and a nucleic acid aptamer attached to the magnetic core, wherein the aptamer has an affinity for a target cell, wherein the magnetic particle conjugate binds to the target cell, wherein the binding of the magnetic particle conjugate to the target cell does not cause activation of the specific biochemical signaling cascade in the target cell; and
   subjecting the magnetic particle conjugate to a magnetic field, wherein application of the magnetic field causes an energy transfer from the magnetic field to the magnetic particle conjugate to the target cell activating a specific biochemical signaling cascade in the target cell, wherein activating cell signaling is caused by transferring energy from the magnetic field to the magnetic particle conjugate and inducing a conformational change in the target cell, wherein subjecting the magnetic particle conjugate to a magnetic field where the energy transfer from the magnetic particle conjugate to the cell causes hyperthermia that induces the conformational change in the cell surface receptors,
   wherein the magnetic core is selected from the group consisting of: Fe3O4, γFe2O3, αFe2O3, iron sulfide, strontium ferrite, barium ferrite, and cobalt ferrite.

2. The method of claim 1, wherein the target cell includes a cell surface receptor, wherein the conformational change occurs in the cell surface receptor.

3. The method of claim 1, wherein the conformation change in cell surface receptor causes one of the following: apoptosis, cell division, motility, stem cell differentiation, or tissue formation.

4. The method of claim 1, wherein the aptamer has an affinity for cell surface receptors of the target cell.

5. The method of claim 1, wherein the nucleic acid aptamer is selected from the group consisting of aptamers targeting: transforming growth factor-β receptor, vascular endothelial growth factor receptor, bone morphogenic protein receptor, and voltage-gated, ligand-gated or mechanosensitive ion channels.

6. A composition comprising: a magnetic particle conjugate having a magnetic core and a nucleic acid aptamer attached to the magnetic core, wherein the aptamer has an affinity for a target cell, wherein the magnetic core is selected from the group consisting of: γFe$_2$O$_3$ and αFe$_2$O$_3$.

7. The composition of claim 6, wherein the nucleic acid aptamer is selected from the group consisting of aptamers targeting: transforming growth factor-β receptor, vascular endothelial growth factor receptor, bone morphogenic protein receptor, and voltage-gated, ligand-gated or mechanosensitive ion channels.

8. The composition of claim 6, wherein the nucleic acid aptamer is selected from the group consisting of aptamers targeting: bone morphogenic protein receptor, and voltage-gated, ligand-gated or mechanosensitive ion channels.

* * * * *